United States Patent [19]

Bolscher

[11] Patent Number: 5,192,285

[45] Date of Patent: Mar. 9, 1993

[54] METHOD FOR INSERTION OF A TRANSPONDER INTO A LIVING BEING

[75] Inventor: Jeroen J. M. Bolscher, Ootmarsum, Netherlands

[73] Assignee: Texas Instruments Incorporated, Dallas, Tex.

[21] Appl. No.: 773,060

[22] Filed: Oct. 8, 1991

[30] Foreign Application Priority Data

Oct. 8, 1990 [NL] Netherlands ............................ 9002183

[51] Int. Cl.⁵ .............................................. A61D 7/00
[52] U.S. Cl. ..................................... 606/117; 606/116; 128/898
[58] Field of Search .................. 606/116, 117; 128/898

[56] References Cited

U.S. PATENT DOCUMENTS

| | | | |
|---|---|---|---|
| 4,065,753 | 12/1977 | Paul | 606/116 |
| 4,083,364 | 4/1978 | Kelly et al. | 606/116 |
| 4,787,384 | 11/1988 | Campbell et al. | 606/117 |
| 4,909,250 | 3/1990 | Smith | 606/117 |
| 5,002,548 | 3/1991 | Campbell et al. | 606/116 |

FOREIGN PATENT DOCUMENTS

| | | | |
|---|---|---|---|
| 0364044 | 4/1990 | European Pat. Off. | 606/117 |
| 8701027 | 11/1988 | Netherlands | 606/117 |

Primary Examiner—Stephen C. Pellegrino
Assistant Examiner—Glenn Dawson
Attorney, Agent, or Firm—Rebecca A. Mapstone; James C. Kesterson; Richard L. Donaldson

[57] ABSTRACT

Method for inserting of a transponder into a living being using a guide. Introduction of the transponder is effected near the base of the ear. The guide (needle) is inserted in a position into the skin being situated between the base of the ear flap and the part of the triangular piece of cartilage (the cartilago scutiformis) lying closest to the skin.

5 Claims, 2 Drawing Sheets

METHOD FOR INSERTION OF A TRANSPONDER INTO A LIVING BEING

FIELD OF THE INVENTION

The present invention relates to a method for insertion of a transponder into a living being using a guide near the base of the ear.

BACKGROUND OF THE INVENTION

Transponders are inserted into living beings for the purpose of being able to identify them. A transponder is a transmitter-receiver unit with a memory accommodated in a housing. When the antenna belonging to it is radiated from outside, the stored data are sent out by the transmitter unit, so that remote identification of the animals in question can take place. The stored data are unique for each animal through the coding used. Guns provided with a needle-shaped guide are generally used for the insertion of transponders. An opening is made in the skin in one way or another with said needle-shaped guide, following which the guide is inserted further into the body of the animal in question. The transponder is then ejected by the guide, either by means of a bar or by means of fluid pressure.

One method of injection discloses in particular an insertion point for living beings, such as pigs, behind the ear. Although this method of insertion was found to be satisfactory for many animals, it was found that it was unsuitable for animals with moving ears, such as cattle. Unlike pigs, cattle move their ears to a considerable extent, and such animals also have the habit of rubbing their heads along bars of feeder units and the like. These movements cause damage to the transponder and/or force it out of the body. There is also the disadvantage of the transponder being relatively easily accessible.

SUMMARY OF THE INVENTION

The object of the present application is to avoid these disadvantages and to provide an insertion point for transponders for cattle.

This object is achieved in the case of a method described above in that the insertion point of the guide into the skin is situated between the base of the earflap and the part of the triangular piece of cartilage lying closest to the skin (the cartilago scutiformis). This triangular piece of cartilage or scutiform cartilage is a typical phenomenon in cattle. It is a loose part and is situated on the top side of the base of the ear. It is surrounded by the muscles of the earflap and the masticatory muscles. The triangular piece of cartilage can be felt easily from the outside and lies with the base against the skull and with the tip against the earflap. The triangular piece of cartilage is easy to find by feeling the animal in the area around the earflap, so that the insertion point is established unequivocally.

It has been found that, when the transponder is inserted in place, movements of the ear and rubbing of the head along bars and other rough objects does not have any effect on movement away of the transponder.

Terms such as in front of and behind etc. in the description and claims must be understood as based on the position of the animal.

DETAILED DESCRIPTION OF THE PREFERRED EMBODIMENTS

According to an advantageous embodiment, the insertion direction of the guide is essentially parallel to the triangular piece of cartilage.

The position of the transponder under the triangular piece of cartilage can be any imaginable one. In order to achieve this, the direction of the guide can vary from perpendicular to the lengthwise direction of the living being to essentially parallel to the lengthwise direction of the living being. Fitting the transponder perpendicular to the living being has the advantage that reading thereof is easier if one is near the animal. On the other hand, there is the risk, in particular in the case of young animals, of the skull being hit. In order to avoid this, it is preferable to insert the guide parallel to the lengthwise direction of the animal. In all cases the insertion path of the guide extends under the triangular piece of cartilage. The insertion point of the transponder preferably lies past the triangular piece of cartilage in line with the insertion path of the guide. In this position it has been found that the transponder will not start to "stray", even a long time after placing. This means that after slaughter of the animal it is extremely simple to find the transponder, and it is ensured that the latter is not in different a place. In this way the transponder is also fitted in a place which cannot be felt, and which is extremely difficult to reach if the animal is still alive. This prevents fraud with transponders. The insertion point of the guide into the skin is preferably situated on or in front of the central axis of the earflap.

BRIEF DESCRIPTION OF THE DRAWINGS

The invention will be explained below in greater detail with reference to an example of an embodiment shown in the drawing, in which:

In FIG. 1 the head of an animal is indicated in its entirety by 1. The ear is indicated by 2, and the insertion point for a transponder is indicated by 3. This is illustrated again in FIG. 2, which is a top view of FIG. 1. The triangular piece of cartilage is indicated schematically therein by 4. This is also known by the names of "scutilum" and "scutiform cartilage". This triangular piece of cartilage 4 extends approximately parallel to the skin between the base of the earflap and the skull. The cartilage of the earflap is indicated by 8. This is also illustrated in FIG. 3. This figure shows an injector 5 provided with an insertion needle 6 for transponders 7. The injector 5 is inserted into the skin in front of the central axis of the earflap. The transponder is shown in the brought-out position, i.e. in the final position. It can be seen that it is provided extremely well protected, a little past the triangular piece of cartilage 4. It has been found that when the transponder is fitted in this way it does not become lost if the animal moves, for example between bars of a feeder unit, and when it flaps over its ears on moving back. Owing to the relatively protected place, it is also difficult to remove the transponder from the living being for fraudulent purposes. Fitting it in the head part means that automatic recognition is possible at automatic feeder stations. In this way, when the animal approaches the feed supply point it is possible to set the feed supply in operation by means of electronic recognition. On the other hand, after slaughtering it is simple to find the transponder again. It has been found that the transponder does not shift during the life of the animal. The transponder can be removed here when the ear of the animal is cut off. The tissue in which the transponder is fitted and the tissue directly surrounding it is not used directly for human consumption, but only after further processing. Consequently the value of the carcass is not adversely affected, and the chance of the transponder inadvertently going into the human consumption circuit on slaughter is minimal. The insertion position is shown essentially at right angles to the longitudinal axis of the animal here, but it must be understood that it is important only that the transponder should be under the triangular piece of cartilage. The needle 6 can therefore also be inserted in other positions, up to parallel to the lengthwise direction of the animal.

Figure 1:
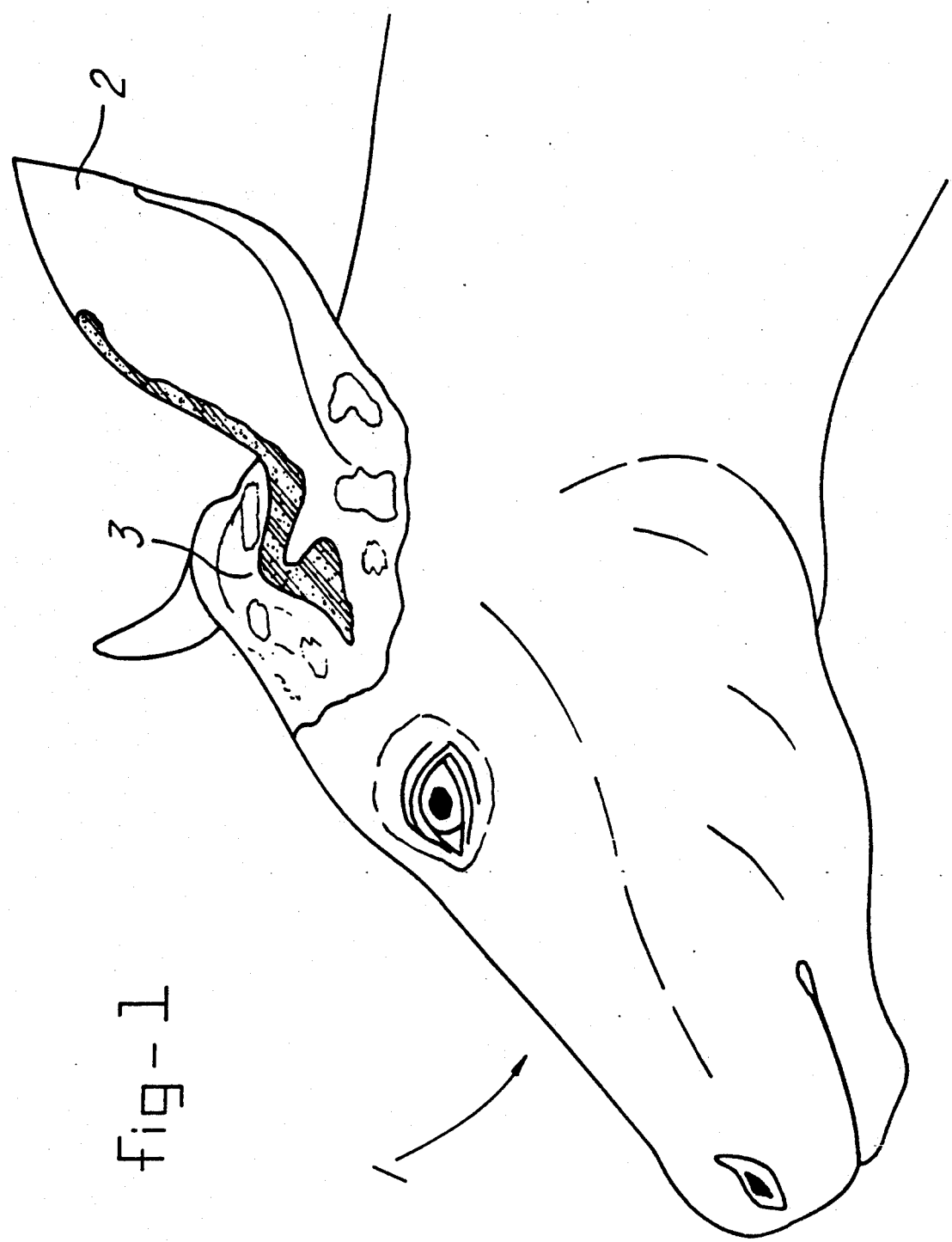
FIG. 1 shows the head of an animal in side view.
Figure 2:
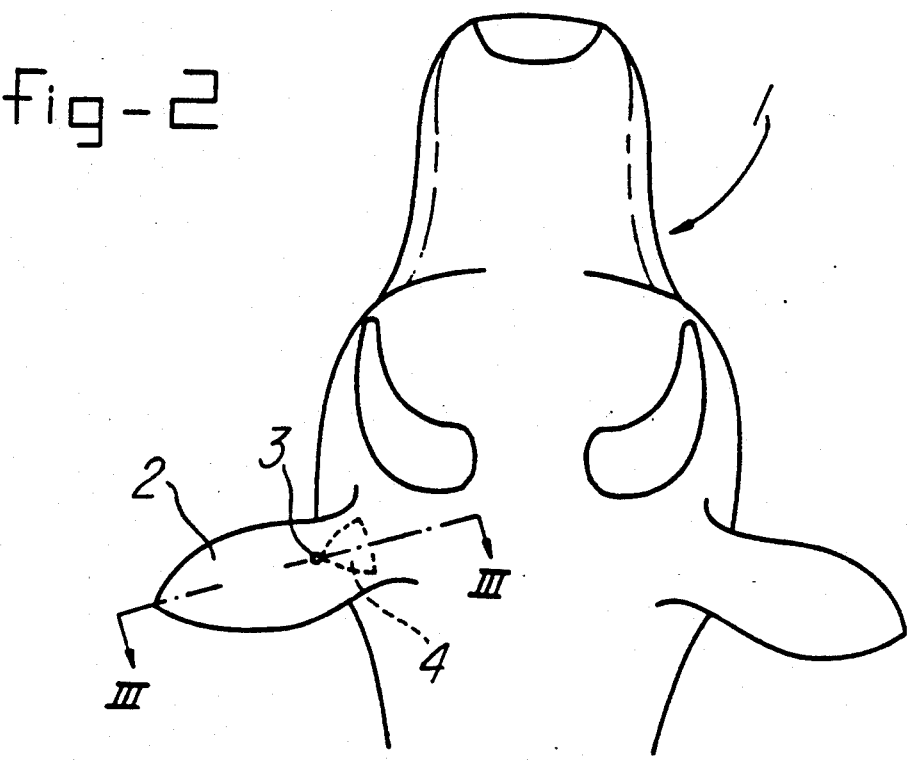
FIG. 2 shows the head from FIG. 1 in top view.
Figure 3:
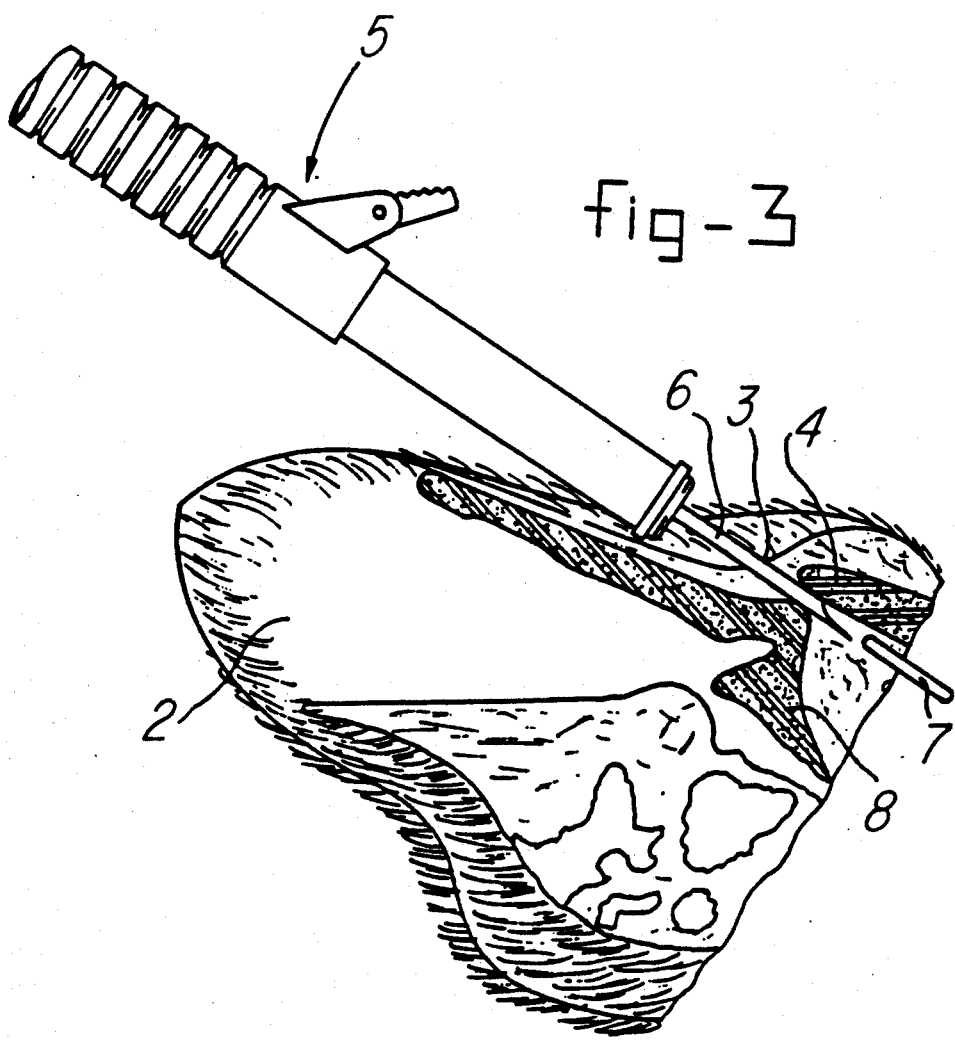
FIG. 3 shows a cross-section along the line III—III in FIG. 2, the insertion of a transponder also being shown schematically.

Although the insertion point described above is preferred, it must be understood that numerous modifications which lie within the scope of the appended claims can be made.

I claim:

1. A method for insertion of an object into an animal having a lengthwise direction, said animal having ears, and earflaps having frontsides and backsides and central axes, and having cartilago scutiformis which lies along the frontside of the central axis of said earflaps and a base wherein said ears attach to said animal, said method comprising the steps of: inserting a needle-shaped guide along an insertion path to a point lying beneath the cartilago scutiformis and injecting said object with said guide such that said object is lodged beneath the cartilago scutiformis to protect said object from damage or migration.

2. A method according to claim 1, wherein the insertion path of said guide is essentially parallel to said cartilago scutiformis.

3. A method according to claim 1, wherein the insertion path of said guide is essentially parallel to said lengthwise direction of said animal.

4. A method according to claim 1, wherein the insertion path of said guide is essentially perpendicular to said lengthwise direction of said animal.

5. A method according to claim 1, wherein the guide is inserted into the skin from the frontside of the central axis of said earflap.

* * * * *